(12) United States Patent
Knight et al.

(10) Patent No.: US 6,423,549 B1
(45) Date of Patent: Jul. 23, 2002

(54) PHYCOERYTHRIN LABELED THYRONINE ANALOGUES AND ASSAYS USING LABELED ANALOGUES

(75) Inventors: Tim Knight; Renato B. Del Rosario, both of Benicia, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 09/808,907

(22) Filed: Mar. 14, 2001

(51) Int. Cl.[7] ............... G01N 33/533; G01N 33/553; G01N 33/78
(52) U.S. Cl. ............ 436/500; 436/526; 436/546
(58) Field of Search ................ 436/546, 526, 436/500

(56) References Cited

U.S. PATENT DOCUMENTS

| | | | |
|---|---|---|---|
| 4,711,855 A | * | 12/1987 | Feinberg |
| 4,741,897 A | * | 5/1988 | Andrews et al. |
| 4,820,860 A | * | 4/1989 | Wissmann et al. |
| 4,859,582 A | * | 8/1989 | Stryer et al. |
| 5,527,709 A | * | 6/1996 | Danielson et al. |
| 5,691,456 A | * | 11/1997 | Adamczyk et al. |

FOREIGN PATENT DOCUMENTS

| | | | |
|---|---|---|---|
| WO | 99/00353 | * | 1/1999 |
| WO | 01/79844 A2 | * | 10/2001 |

OTHER PUBLICATIONS

Khosravi et al, Clin. Chem. 39: 256–262 (1993).*
Piran et al, J. Immunol. Methods 133: 207–214 (1990).*
Law et al, J. Bioluminescence and Chemiluminescence 4:; 88–98 (1989).*
Chopra, Thyroid 8: 249–257 (1998).*

* cited by examiner

*Primary Examiner*—Mary E. Ceperley
(74) *Attorney, Agent, or Firm*—Townsend and Townsend and Crew LLP (57) ABSTRACT

The invention provides fluorescent analogues of thyroid hormones $T_3$ and $T_4$. Also provided are assays for thyroid hormones utilizing the compounds of the invention. The assays of the invention are in both one-step and two-step formats and allow the determination of both $T_3$ and $T_4$ concentration in a sample.

11 Claims, 8 Drawing Sheets

PHYCOERYTHRIN LABELED THYRONINE ANALOGUES AND ASSAYS USING LABELED ANALOGUES

FIELD OF THE INVENTION

This invention resides in the field of clinical assays indicative of biological conditions, and is of interest in the technology of binding assays for analytes in biological fluids for purposes of diagnosis, monitoring, or other clinical functions.

DESCRIPTION OF THE PRIOR ART

Since the initial disclosure of radioimmunoassays in 1961, a wide variety of in vitro assays using affinity-type binding have been developed. Variations include the type of binding (for example, specific vs. non-specific, and immunological vs. non-immunological), the type of detection (including the use of labels such as enzyme labels, radioactive labels, fluorescent labels, and chemiluminescent labels), methods of detecting whether or not binding has occurred (including methods in which bound species are separated from unbound species and methods that do not include such separation), and various other aspects of the assay procedure. The technology is currently used for the detection and quantitation of countless species, and serves as an analytical tool in the detection and monitoring of many physiological conditions and functions and the diagnosis and treatment of many diseases.

Of particular interest are assays that determine thyroid hormone levels. Accurate assessment of thyroid hormone levels is critical to determining thyroid function status. The free fraction of thyroid hormone in serum is only about 0.03% for thyroxin ($T_4$) (I) and about 0.3% for 3,5,3'-triiodothyronine ($T_3$) (II). Many methods have been developed for measuring serum thyroid hormone content, including labeled analogue-radioimmunoassay, ultrafiltration, column fractionation, and direct equilibrium dialysis followed by radioimmunoassay (Kapstein et al., *J. Clin. Endocrin. Metab.* 52: 1073–1079 (1981)).

Although radioimmunoassays are of use in determining thyroid hormones in serum, there has been an effort by both industry and academia to replace radioisotopes with non-isotopic labels in clinical assays. Thyroid hormone assays that use non-radioactive analogues of thyroid hormones have been developed. For example, assays relying on fluorescent thyroid hormone analogues (Khosravi et al., *Clin. Chem.* 39: 256–262 (1993); Piran et al., *J. Immunol. Methods* 133: 207–214 (1990); Adamczyk et al., U.S. Pat. No. 5,691,456)) and chemiluminescent thyroid hormone analogues (Law et al., *J. Bioluminescence and Chemiluminescence* 4: 88–98 (1989)) to generate a signal are known in the art.

Numerous thyronine derivatives that include a detectable label within their framework are known in the art. The labeled thyronine derivatives are slight modifications of the phenyl ether nucleus of thyronine. For example, Wissman et al. (U.S. Pat. No. 4,820,860) disclose thyronine derivatives in which an iodine substituent on the thyronine nucleus is replaced by a moiety that includes a detectable label. Danielson et al. (U.S. Pat. No. 5,527,709) disclose an immunoassay using a label that includes a thyronine nucleus tethered to a detectable labeling group by means of a linking chain. U.S. Pat. No. 4,741,897, to Andrews et al. discloses compounds in which the thyronine nucleus is modified by attaching a linking group having a iodinatable aryl or heteroaryl group bound thereto. Other references disclosing compounds having a derivatized thyronine nucleus include, Feinberg (U.S. Pat. No. 4,711,855); Adamczyk et al., (U.S. Pat. No. 5,691,456, and *Bioconjugate Chem.* 5: 459–462 (1994)). To produce each of the agents disclosed in the above-enumerated references, the thyronine nucleus must be obtained and its integrity maintained during subsequent synthetic elaboration to produce the thyronine derivatives.

Fluorescent and chemiluminescent assays for thyroid hormones typically measure only serum $T_4$ content. Assays in which both $T_3$ and $T_4$ are measured are important to the appropriate diagnosis and treatment of thyroid disease. Thus, efforts have been directed to developing assays that measure both serum $T_3$ and $T_4$ levels. With the exception of certain radioisotopic methods (see, Chopra, *Thyroid* 8: 249–257 (1998)), assays that are also capable of measuring $T_3$ content require a separate assay mixture and a separate probe for measuring $T_3$. Each additional assay probe, mixture and step adds additional expense and requires additional effort by technical staff. Thus, a non-radioactive immunoassay that detected both $T_3$ and $T_4$ levels in serum using a single assay mixture would represent a significant advance in the field. An even further advance would result from the use of detectable assay probes that were structurally simple and could be easily and inexpensively prepared.

SUMMARY OF THE INVENTION

It has now been discovered that structurally simple fluorescent analogues of thyroid hormones in which the thyronine nucleus is replaced by a monocyclic phenol moiety cross-react with antibodies raised against the thyroid hormones $T_3$ and $T_4$, and are useful in immunoassays for detecting $T_3$ and $T_4$. The new fluorescent analogues are easily prepared from readily available, inexpensive starting materials. The presence of a highly fluorescent label (e.g., phycobiliprotein) within the structure of the compounds of the invention allows their detection at low concentrations Thus, in a first aspect, the present invention provides $T_3$ and $T_4$ thyroid hormone analogues that are labeled with a highly fluorescent phycobiliprotein. The fluorescent hormone analogues are easily prepared and characterized. Furthermore, the fluorescent hormone analogues interact with antibodies raised against $T_3$ and $T_4$ and compete with these hormones for the antibody hapten binding site.

The compounds of the invention have structures according to Formulae III–VI, below:

in which PBP is a phycobiliprotein.

In a second aspect, this invention provides an immunoassay for individually determining $T_3$ and $T_4$ thyroid hormones in a sample using one or more compound of the invention. The immunoassay includes, forming an assay mixture by contacting the biological sample with a plurality of microparticles and a fluorescent thyroid hormone analogue of the invention. The microparticles are classifiable into a first population and a second population, which are distinguishable from each other by an automated detection means. The first population of microparticles has an anti-$T_3$ antibody coupled to the particles. The second population of microparticles has an anti-$T_4$ antibody coupled to the particles. In one embodiment, the fluorescent thyroid hormone analogue has a structure according to Formula V. Alternatively, the fluorescent analogue is a mixture of compounds according to Formula III and one of compound IV or VI. The particles are then recovered from the assay mixture and the fluorescence from the first and second populations is detected, thereby determining the amount of $T_3$ thyroid hormone and $T_4$ thyroid hormone in the biological sample.

These and other features and advantages of the invention will be more readily understood by the description that follows.

BRIEF DESCRIPTION OF THE DRAWINGS

FIG. 1 is a graphical display of data collected during an assay in which the concentration of $T_3$ and $T_4$ in a sample were determined simultaneously using a single fluorescent thyroid hormone analogue according to Formula V: (A) fluorescence units vs. concentration of free $T_3$; (B) fluorescence units vs. concentration of free $T_4$.

FIG. 2 is a graphical display of data collected during an assay in which the concentrations of $T_3$ and $T_4$ in a sample were determined simultaneously using two fluorescent thyroid hormone analogues according to Formulae III and VI: (A) fluorescence units vs. concentration of free $T_3$; (B) fluorescence units vs. concentration of free $T_4$.

FIG. 3 is a graphical display of data collected during an assay in which the concentration of $T_3$ and $T_4$ in a sample were determined in a 2-step sequential assay using conjugates according to Formulae III and VI: (A) fluorescence units vs. concentration of free $FT_4$; (B) expansion of plot from (A) from 0.0–2.0 ng $FT_4$/100 mL; (C) fluorescence units vs. concentration of free $FT_3$; (D) expansion of plot from (C) from 0.0–3.0 ng $FT_3$/100 mL.

DETAILED DESCRIPTION OF THE INVENTION AND THE PREFERRED EMBODIMENTS

The present invention provides fluorescent $T_3$ and $T_4$ analogues that are useful in assays for serum $T_3$ and $T_4$ levels. The compounds of the invention are highly fluorescent, preferably by virtue of the presence of a phycobiliprotein within the structure of the compounds. Proteins with bilin prosthetic groups are used as fluorescent labels in a number of systems, including those involving ligand-receptor reactions (Stryer et al., U.S. Pat. No. 4,859,582). The biliproteins are readily conjugated, provide for high quantum efficiency with absorption and emission at long wavelengths in the visible, and enhance the sensitivity and accuracy of fluorescent assay methods.

A. The Compounds

In a first aspect, the present invention provides compounds having structures according to Formulae III–VI:

-continued in which PBP is a phycobiliprotein, preferably phycoerythrin.

The compounds of the invention are prepared by methods known to those of skill in the art. An exemplary reaction scheme for compounds that include the 3,5-diiodotyrosyl moiety within their framework is set forth in Scheme 1.

Scheme 1

In Scheme 1, starting material 1 includes a carboxylic acid in addition to the 3,5-diiodotyrosyl moiety. The carboxylic acid is activated with a dehydrating agent, such as EDC, and subsequently converted to the N-hydroxysuccinimide active ester. The ester is contacted with the phycobiliprotein to afford compound 2, in which the R group may vary according to a particular application. Compounds of the invention that include the 4-hydroxyphenylacetyl moiety within their structural framework, such as compounds of Formula V, are prepared in an analogous manner. Other methods of preparing the compounds set forth in Formnulae III, IV, V and VI, and other compounds of the invention in which the phenyl ring is differently substituted or the linker between the phenyl group and the fluorescent moiety is varied structurally will be apparent to those of skill in the art.

In a second aspect, the present invention provides an immunoassay for detecting $T_3$ and $T_4$ thyroid hormone in a sample using one or more of the compounds of the invention. The immunoassay includes, forming an assay mixture by contacting the biological sample with a plurality of microparticles and a fluorescent thyroid hormone analogue of the invention. The microparticles are classifiable into a first population and a second population, which are distinguishable from each other by an automated detection means. The first population of microparticles has an anti-$T_3$ antibody coupled to the particles. The second population of microparticles has an anti-$T_4$ antibody coupled to the particles. In one embodiment, the fluorescent thyroid hormone analogue has a structure according to Formula V. Alternatively, the fluorescent analogue is a mixture of compounds according to Formula III and one of compound IV or VI. The particles are then recovered from the assay mixture and the fluorescence from the first and second populations is detected, thereby determining the amount of $T_3$ thyroid hormone and $T_4$ thyroid hormone in the biological sample.

The microparticles used in performing the assay of the invention can be prepared from any material that is useful in the context of the immunoassays of the invention. Many binding assays are heterogeneous assays, which rely in part on the transfer of analyte from a liquid sample to a solid phase by the binding of the analyte during the assay to the surface of the solid phase. At some stage of the assay, the sequence of which varies depending on the assay protocol, the solid phase and the liquid phase are separated and the determination leading to detection and/or quantitation of the analyte is performed on one of the two separated phases. One useful type of solid phase is magnetic particles, which offer the combined advantages of a high surface area and the ability to be temporarily immobilized at the wall of the assay receptacle by imposition of a magnetic field while the liquid phase is aspirated, the solid phase is washed, or both. Descriptions of such particles and their use are found in Forrest et al., U.S. Pat. No. 4,141,687 (Technicon Instruments Corporation, Feb. 27, 1979); Ithakissios, U.S. Pat. No. 4,115,534 (Minnesota Mining and Manufacturing Company, Sep. 19, 1978); Vlieger, A.M., et al., *Analytical Biochemistry* 205:1–7 (1992); Dudley, *Journal of Clinical Immunoassay* 14:77–82 (1991); and Smart, *Journal of Clinical Immunoassay* 15:246–251 (1992).

In a presently preferred embodiment, the microparticles used in an assay of the invention includes a magnetically responsive material. The term "magnetically responsive material" is used herein to denote a material that responds to a magnetic field. Magnetically responsive materials useful in the assays of this invention include paramagnetic materials, ferromagnetic materials, ferrimagnetic materials, and metamagnetic materials. Paramagnetic materials are preferred. Examples are iron, nickel, and cobalt, as well as metal oxides such as $Fe_3O_4$, $BaFe_{12}O_{19}$, CoO, NiO, $Mn_2O_3$, $Cr_2O_3$, and CoMnP. Rather than constituting the entire microparticle, the magnetically responsive material is preferably only one component of the microparticle whose remainder consists of a polymeric material to which the magnetically responsive material is affixed and which is chemically derivatized to permit attachment of an anti-$T_3$ or anti-$T_4$ antibody.

Multiplexing with the use of microparticles in accordance with this invention is achieved by assigning the microparticles to two or more groups, each group performing a separate assay and separable from the other group(s) by a "differentiation parameter," which term is used herein to denote a distinguishable characteristic that permits separate detection of the assay result in one group from that in another group. The differentiation parameter is preferably detected by an automated detection means. Differentiation is accomplished by incorporating various fluorescent materials in the particles, the various fluorescent materials having different fluorescent emission spectra and being distinguishable on this basis. See, for example, Chandler et al., U.S. Pat. No. 5,981,180.

Fluorescence can be used both as a means of distinguishing the microparticle populations from each other and as a means of detection for the assay performed on the particle. The use of fluorescent materials with different emission spectra can be used as a means of distinguishing the populations of microparticles from each other and as a means of distinguishing the thyroid hormone identity from the assay detections. Examples of fluorescent substances that can be used as a means of distinguishing groups include, but are not limited to, fluorescein and phycoerythrin. In an exemplary embodiment, different particle groups are dyed with different fluorophores, or concentrations of fluorophores and assay-specific reporters are labeled with phycoerythrin.

Still other examples of a differentiation parameter that can be used to distinguish among the various populations of particles are light scatter, light emission, or combinations of light scatter and emission. Side angle light scatter varies with particle size, granularity, absorbance and surface roughness, while forward angle light scatter is mainly affected by size and refractive index. Thus, varying any of these qualities serves as a means of distinguishing the various particle populations. Light emission can be varied by incorporating fluorescent materials in the microparticles and using fluorescent materials that have different fluorescence intensities or that emit fluorescence at different wavelengths, or by varying the amount of fluorescent material incorporated. By using a plurality of fluorescent emissions at various wavelengths, the wavelength difference can be used to distinguish the particle populations from each other and also to distinguish the labels indicating the occurrence of binding reactions in the assay from the labels that identify the particle populations.

In a preferred embodiment, the microparticles will have two or more fluorochromes incorporated within them so that each microparticle in the array will have at least three distinguishable parameters associated with it, i.e., side scatter together with fluorescent emissions at two separate wavelengths. For example, the microparticle can be made to contain a red fluorochrome such as Cy5 together with an orange fluorochrome such as Cy5.5. Additional fluorochromes can be used to further expand the system. Each microparticle can thus contain a plurality of fluorescent dyes at varying wavelengths. Exemplary particles useful in practicing the invention include, but are not limited to, those disclosed in Chandler et al., U.S. Pat. No. 5,981,180.

Still another example of a differentiation parameter that can be used to distinguish among the various populations of particles is absorbance. When light is applied to microparticles the absorbance of the light by the particles is indicated mostly by the strength of the laterally (side-angle) scattered light while the strength of the forward-scattered light is relatively unaffected. Consequently, the difference in absorbance between various colored dyes associated with the microparticles is determined by observing differences in the strength of the laterally scattered light.

A still further example of a differentiation parameter that can be used to distinguish among the various groups of particles is the number of particles in each population. The number of particles of each population in an assay is varied in a known way, and the count of particles having various assay responses is determined. The various responses are associated with a particular assay by the number of particles having each response.

As the above examples illustrate, a wide array of parameters or characteristics can be used as differentiation parameters to distinguish the microparticles of one population from those of another. The differentiation parameters may arise from particle size, from particle composition, from particle physical characteristics that affect light scattering, from excitable fluorescent dyes or colored dyes that impart different emission spectra and/or scattering characteristics to the microparticles, or from different concentrations of one or more fluorescent dyes. When the distinguishable microparticle parameter is a fluorescent dye or color, it can be coated on the surface of the microparticle, embedded in the microparticle, or bound to the molecules of the microparticle material. Thus, fluorescent microparticles can be manufactured by combining the polymer material with the fluorescent dye, or by impregnating the microparticle with the dye. Microparticles with dyes already incorporated and thereby suitable for use in the present invention are commercially available, from suppliers such as Spherotech, Inc. (Libertyville, Ill., USA) and Molecular Probes, Inc. (Eugene, Oreg., USA), Luminex (Austin, Tex., USA).

In a preferred embodiment, the automated detection technique utilized in the assays of the invention utilize flow cytometry for the detection and analysis of particles and species bound to the particles. Flow cytometry has been disclosed for use in the detection and separation of antigens and antibodies by Coulter Electronics Inc., United Kingdom Patent No. 1,561,042 (published Feb. 13, 1980); and for quantitation of PCR (Polymerase Chain Reaction) products by Vlieger, A.M., et al., *Analytical Biochemistry* 205:1–7 (1992). Flow cytometry has been limited in the analysis of biological samples. The sensitivity of those assay formats that do not require separation of free from bound species (i.e., sandwich and competitive assays) is adversely affected by the increased background signal noise caused by the unbound label. Antigen-capture antibody assays require the removal of non-specific immunoglobulin before the addition of class-specific labeled anti-Ig. Samples containing particulates (such as stool samples, for example) require the removal of this debris which would otherwise interfere with the flow cytometric measurement. Traditional separation techniques, such as filtration or centrifugation can remove unbound label or non-specific Ig but fail to remove interfering particulates from the patient sample. In addition, these traditional separation techniques are difficult and/or costly to automate. The use of magnetic particles and magnetism is a well known method and has been shown to be both efficient and cost-effective in automated diagnostic systems.

In a preferred embodiment, the assay of the invention is a competitive assay. Competitive assays can be performed by using magnetically responsive microparticles to which are bound molecules of a binding protein (such as an antibody) specific for the analyte. During the assay, the sample and a quantity of labeled analyte analogue, either simultaneously or sequentially, are mixed with the microparticles. By using a limited number of binding sites on the microparticles, the assay causes competition between the labeled analyte analogue and the analyte in the sample for the available binding sites. After a suitable incubation period, the mixture of liquid and solid is placed under the influence of a magnetic field, causing the microparticles to adhere to the walls of the reaction vessel, and the liquid phase is removed. The microparticles, still adhering to the vessel wall, are then washed to remove any remaining unbound analyte and labeled analyte analogue, and resuspended in a carrier liquid for introduction into a flow cytometer where the microparticles are classified by size, color or other parameter and the label is detected.

Immunometric or sandwich assays, as another example, are performed by using magnetically responsive microparticles to which are bound antibodies to the analyte. In this case, the bound antibodies are present in excess relative to the suspected quantity range of the analyte so that all of the analyte binds. The microparticles are placed in contact with the sample, and simultaneously or sequentially, a second antibody to the same analyte is added, again in excess relative to the analyte, the first and second antibodies binding different epitopes on the analyte in a non-interfering manner, and the second antibody being conjugated to a detectable label. After a suitable incubation period, the liquid mixture with microparticles suspended therein is placed under the influence of a magnetic field, causing the microparticles to adhere to the walls of the reaction vessel, and the liquid phase is removed. The microparticles, still adhering to the vessel wall, are then washed to remove excess amounts of the second, labeled antibody that have not become bound to the immobilized analyte, and the microparticles are then resuspended in a carrier liquid for introduction into a flow cytometer where they are sorted by size and the label detected. An example of an analyte that is readily detected in this manner is thyroid stimulating hormone (TSH). The label on the second antibody can again be phycoerythrin.

In one aspect, this invention combines multiplexing of heterogeneous binding assays of a single fluid sample by flow cytometry with the use of solid magnetic particles as the solid phase to facilitate the separation of solid and liquid phases. The magnetic particles have sizes that are microscopic (and hence termed "microparticles") and that are classifiable into populations according to distinguishable characteristics or differentiation parameters. The groups are substantially discrete (nonoverlapping), with the mean values of the distinguishing characteristics of adjacent groups sufficiently far apart to permit differentiation of each group from the others by conventional automated detection methods. An assay reagent (e.g., an antibody) is bonded to each particle, with substantially all particles within each group bearing the same assay reagent and with different assay reagents from one group to the next. The groups are thus distinguishable not only by their distinctive differentiation parameters for purposes of differentiation but also by the assay reagents bonded to the particles such that all particles in each group take part in a distinct binding assay, and do so in a selective manner relative to the assay reagents bonded to particles in other populations.

This aspect of the invention further resides in a combination of solid particles for use in the multiplex assay described in the preceding paragraph, the particles being of magnetically responsive material and having a particular detectable parameter that encompasses a range of values that differentiate the particles into two or more substantially discrete groups that are distinguishable by automated detection methods that are appropriate for the particular parameter.

The magnetic character of the particles permits the automated separation of solid phase from liquid phase at a point in the sequence of the assay that is preferably prior to the stage at which the particle groups are differentiated according to the differentiation parameter. The separation can serve any of a variety of purposes, including the removal of sample debris from the assay components, the removal of sample components that would otherwise contribute significantly to the background noise at the detection stage, the removal of competing binding members that are not the subject of any of the assays but would otherwise interfere with the results, and the removal of bound from unbound species such as labels, analytes, analyte binding members, and label-binding member conjugates. The particular function in any given assay or combination of assays will depend on the nature of the assay and the assay protocol.

Methods of and instrumentation for flow cytometry are known in the art, and those that are known can be used in the practice of the present invention. Flow cytometry in general resides in the passage of a suspension of the microparticles as a stream past a light beam and electro-optical sensors, in such a manner that only one particle at a time passes through the region. As each particle passes this region, the light beam is perturbed by the presence of the particle, and the resulting scattered and fluorescent light are detected. The optical signals are used by the instrumentation to identify the subgroup to which each particle belongs, along with the presence and amount of label, so that individual assay results are achieved. Descriptions of instrumentation and methods for flow cytometry are found in the literature. Examples are McHugh, "Flow Microsphere Immunoassay for the Quantitative and Simultaneous Detection of Multiple Soluble Analytes," *Methods in Cell Biology* 42, Part B (Academic Press, 1994); McHugh et al., "Microsphere-Based Fluorescence Immunoassays Using Flow Cytometry Instrumentation," *Clinical Flow Cytometry*, Bauer, K. D., et al., eds. (Baltimore, Md., USA: Williams and Williams, 1993), pp. 535–544; Lindmo et al., "Immunometric Assay Using Mixtures of Two Particle Types of Different Affinity," *J. Immunol. Meth.* 126: 183–189 (1990); McHugh, "Flow Cytometry and the Application of Microsphere-Based Fluorescence Immunoassays," *Immunochemica* 5: 116 (1991); Horan et al., "Fluid Phase Particle Fluorescence Analysis: Rheumatoid Factor Specificity Evaluated by Laser Flow Cytophotometry," *Immunoassays in the Clinical Laboratory*, 185–189 (Liss 1979); Wilson et al., "A New Microsphere-Based Immunofluorescence Assay Using Flow Cytometry," *J. Immunol. Meth.* 107: 225–230 (1988); Fulwyler et al., "Flow Microsphere Immunoassay for the Quantitative and Simultaneous Detection of Multiple Soluble Analytes," *Meth. Cell Biol.* 33: 613–629 (1990); Coulter Electronics Inc., United Kingdom Patent No. 1,561,042 (published Feb. 13, 1980); and Steinkamp et al., *Review of Scientific Instruments* 44(9): 1301–1310 (1973). A list of vendors of flow cytometric products can be found on the Internet at www.molbio.princeton.edu/facs/FCMsites.html.

Similarly, methods of and instrumentation for applying and removing a magnetic field as part of an automated assay are known to those skilled in the art and reported in the literature. Examples of literature reports are the Forrest et al. patent, the Ithakissios patent, the Vlieger et al. paper, the Dudley paper and the Smart paper, all referenced above.

The materials, methods and devices of the present invention are further illustrated by the examples which follow. These examples are offered to illustrate, but not to limit the claimed invention.

EXAMPLES

Example 1 describes the synthesis of representative phycoerythrin conjugates of the invention. Example 2 describes an assay of the invention in which both $FT_3$ and $FT_4$ are measured in a single step using a single phycoerythrin conjugate of the invention. Example 3 describes an assay of the invention in which both $FT_3$ and $FT_4$ are measured in a single step utilizing two phycoerythrin conjugates of the invention. Example 4 describes an assay of the invention in which $FT_3$ and $FT_4$ are measured sequentially using two different conjugates of the invention.

Example 1

1.1 Synthesis of FMOC-3,5-diiodotyrosyl Phycoerythrin Conjugate (III)

To 6.0 mg (0.031 mmol) of EDC.HCl was added 175 μL (0.016 mmol) of a DMF solution (10.5 mg/175 μL) of N-Fmoc-3,5-diiodotyrosine (Aldrich Chemical Co.) followed by 64 μL (0.033 mmol) of a DMF solution (22.9 mg/381.7 μL) of N-hydroxysuccinimide (Pierce Chemical Co.). The mixture was vortexed vigorously until the solid was completely dissolved and then it was agitated for 75 min. An aliquot of the above reaction mixture (12 μL) was then added to a solution of 2 mg (4.2 μmol) of β-phycoerythrin (Cyanotech) in 0.05M PBS (228 μL) and the conjugation mixture was gently agitated overnight at ambient temperature in the dark. After this period, the reaction mixture was purified by gravity gel filtration chromatography (Sephadex G-75, eluent: 50 mM PBS, column: Bio-Rad Econo 1.5×30 cm; detection: Bio-Rad EM-1 Econo UV Monitor, λ280 nm). The desired pink-red conjugate fractions were pooled together and stored at 4° C.

1.2 Synthesis of 3-Chloro-4-hydroxyphenylacetyl-Phycoerythrin Conjugate (V)

To 6.0 mg (0.031 mmol) of EDC.HCl was added 52 μl (0.016 mmol) of a DMF solution (15.9 mg/265 μL) of 3-chloro-4-hydroxyphenylacetic acid (Aldrich Chemical Co.) followed by 64 μL (0.033 mmol) of a DMF solution (12.7 mg/211.7 μL) of N-hydroxysuccinimide (Pierce Chemical Co.). The mixture was vortexed vigorously until complete dissolution and agitated for 75 min. An aliquot of the above reaction mixture (12 μL) was then added to a solution of 2 mg (4.2 μmol) of β-phycoerythrin (Cyanotech) in 0.05M PBS (228 μL) and the conjugation mixture was gently agitated overnight at ambient temperature in the dark. After this period, the reaction mixture was purified by gravity gel filtration chromatography (Sephadex G-75, eluent: 50 mM PBS, column: Bio-Rad Econo 1.5×30 cm; detection: Bio-Rad EM-1 Econo UV Monitor, λ280 nm). The desired pink-red conjugate fractions were pooled together and stored at 4° C.

1.3 Synthesis of N-Acetyl-3-iodotyrosyl phycoerythrin Conjugate (VI)

To 6.0 mg (0.031 mmol) of EDC.HCl was added 100 μL (0.017 mmol) of a DMF solution (10 mg/170 μL) of N-acetyl-3-iodotyrosine (Aldrich Chemical Co.) followed by 65 μL (0.033 mmol) of a DMF solution (42.9 mg/715 μL) of N-hydroxysuccinimide (Pierce Chemical Co.). The mixture was vortexed vigorously until the solid is completely dissolved and then agitated for 75 min. An aliquot of the above reaction mixture (12 μL) was then added to a solution of 2 mg (4.2 μmol) of β-phycoerythrin (Cyanotech) in 0.05M PBS (228 μL). The resulting conjugation mixture was gently agitated overnight at ambient temperature in the dark. After this period, the reaction mixture was purified by gravity gel filtration chromatography (Sephadex G-75, eluent: 50 mM PBS, column: Bio-Rad Econo 1.55×30 cm; detection: Bio-Rad EM-1 Econo UV Monitor, λ280 nm). The desired pink-red conjugate fractions were pooled together and stored at 4° C.

Example 2

Example 2 describes the assay of a sample for both $T_3$ and $T_4$ using a single phycoerythrin conjugate. The microparticles used in the invention are coated with either anti-$T_3$ or anti-$T_4$ antibody. The wash buffer consists of 50 mM PBS, 0.5% BGG, 0.1% $NaN_3$ and 0.1% Tween at pH 7.4. The concentrations of stock solutions of the conjugates of the invention were determined by UV spectroscopy (545 nm, $\lambda_{max}$ of β-phycoerythrin) using an extinction coefficient of $2.41 \times 10^6$ for β-phycoerythrin.

2a $T_3$ and $T_4$ Assay

To 100 μL sample, 100 μL of the reagent particles (Micromod 8 μm, (a) 7.5 μg/cm² anti-$T_3$ antibody; (b) 4 μ/cm² anti-$T_4$ antibody) were added. The resulting mixture was incubated 15 minutes at 37° C. with agitation. The particles were subjected to a magnetic field for 3 minutes, following which the fluid was removed by aspiration. To the particles were added 300 μL wash buffer. The particles were again subjected to a magnetic field and the wash buffer was removed by aspiration. The treatment with wash buffer was repeated twice, after which the particles were magnetically separated from the wash buffer, which was removed by aspiration.

To the particles prepared as described above, 3-chloro-4-hydroxyphenyl acetic acid conjugate (50 μL) was added. The conjugate was added as a stock solution ($1.7 \times 10^{-6}$ M) diluted 1:40 with 50 mM PBS, 0.5% BGG, 2.75% PEG 8000, 0.1% $NaN_3$ and 0.1% Tween, at pH 7.4. The resulting mixture was incubated for 15 minutes at 37° C. with agitation. The mixture was magnetically separated for 3 minutes and the fluid was removed by aspiration. To the particles, wash buffer (300 μL) was added. The particles were submitted to a cycle of magnetic separation and the fluid was removed by aspiration. The wash process was repeated twice. The particles were suspended in wash buffer (35 μL) and read on a Luminex LX100.

2b Results

Figure 1A:
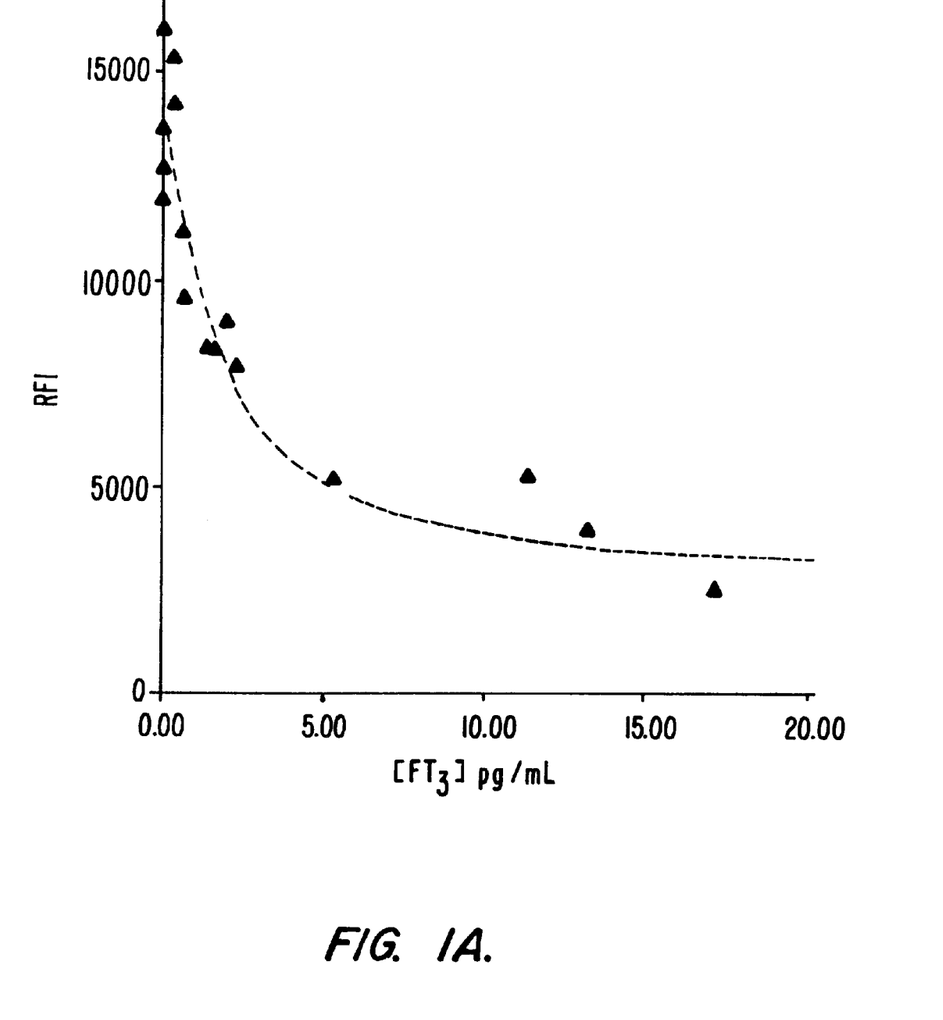
Figure 1B:
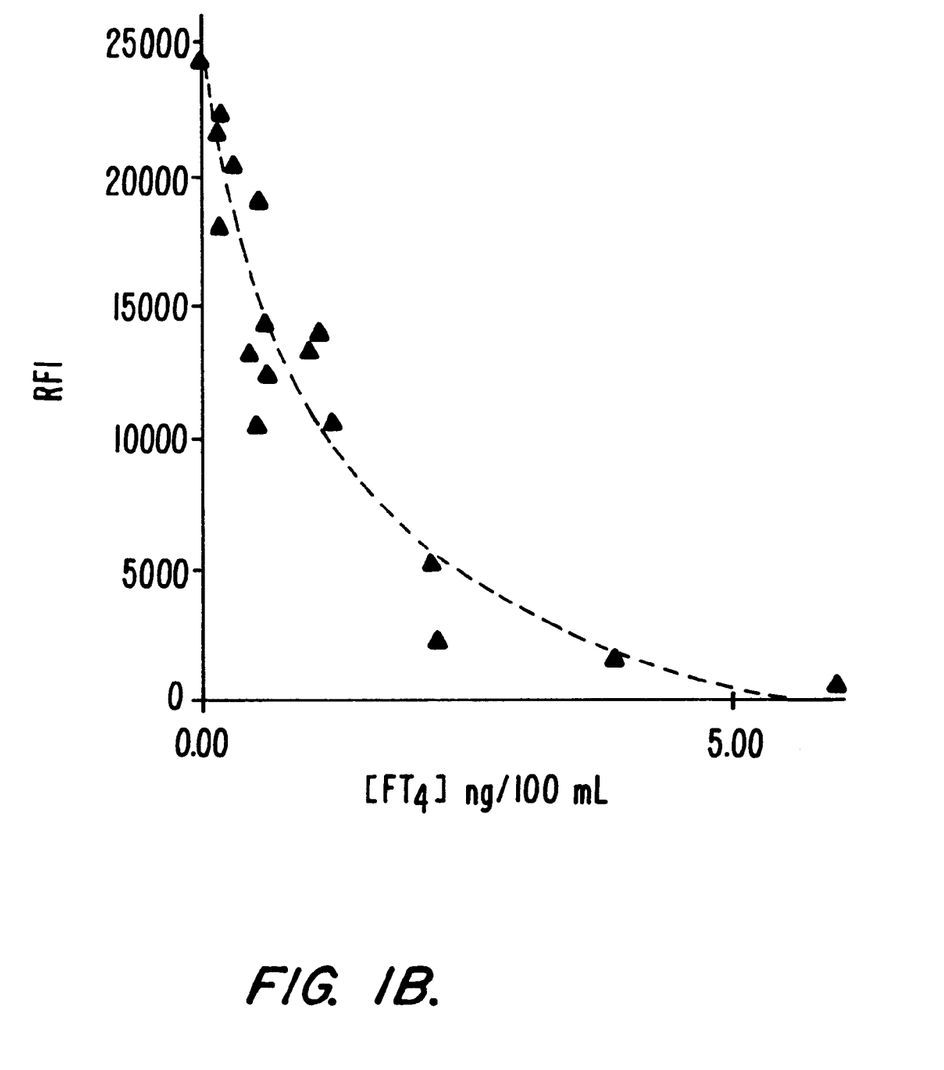

The results of the single conjugate assay for $T_3$ are set forth graphically in FIG. 1A. Table 1 sets forth results for the $T_3$ content of the sample as determined by a method of the invention, and provide a comparison with a radioactive immunoassay technique (RIA). The results for the T4 assays are set forth graphically in FIG. 1B. Table 2 sets forth results for the $T_4$ content of the sample as determined by a method of the invention, and provide a comparison with a radioactive immunoassay technique (RIA).

TABLE 1

| DPC RIA | Rep 1 | Rep 2 | Mean | % CV | pg/mL | B/Bo |
|---|---|---|---|---|---|---|
| 0.41 | 14557 | 13982 | 14270 | 2.8% | #NUM! | 1.194 |
| 0.03 | 14081 | 13383 | 13732 | 3.6% | 0.1 | 1.149 |
| 0.00 | 12957 | 12488 | 12722 | 2.6% | 0.3 | 1.065 |
| 0.68 | 11163 | 11208 | 11186 | 0.3% | 0.7 | 0.936 |
| 0.05 | 16660 | 15462 | 16061 | 5.3% | #NUM! | 1.344 |
| 0.34 | 15623 | 15186 | 15405 | 2.0% | #NUM! | 1.289 |
| 1.43 | 8558 | 8196 | 8377 | 3.1% | 1.7 | 0.701 |
| 1.99 | 9125 | 8913 | 9019 | 1.7% | 1.5 | 0.755 |
| 17.08 | 2547 | 2660 | 2603 | 3.1% | #NUM! | 0.218 |
| 11.35 | 5224 | 5376 | 5300 | 2.0% | 4.6 | 0.443 |
| 1.65 | 8317 | 8370 | 8343 | 0.4% | 1.8 | 0.698 |
| 2.33 | 8003 | 7819 | 7911 | 1.6% | 2.0 | 0.662 |
| 13.19 | 4031 | 3974 | 4002 | 1.0% | 9.1 | 0.335 |
| 0.69 | 9859 | 9477 | 9668 | 2.8% | 1.2 | 0.809 |
| 0.63 | 10075 | 9161 | 9618 | 6.7% | 1.2 | 0.805 |
| 5.32 | 5148 | 5231 | 5190 | 1.1% | 4.8 | 0.434 |
| 0.00 | 11982 | 11921 | 11951 | 0.4% | 0.5 | 1.000 |

TABLE 2

| DPC RIA | Rep 1 | Rep 2 | Mean | % CV | [FT4] ng/100 mL | B/Bo |
|---|---|---|---|---|---|---|
| 0.52 | 19454 | 18465 | 189.19 | 3.7% | 0.2 | 0.780 |
| 0.29 | 20620 | 20157 | 20389 | 1.6% | 0.2 | 0.839 |
| 0.15 | 18414 | 17545 | 17979 | 3.4% | 0.3 | 0.740 |
| 0.59 | 14154 | 14370 | 14262 | 1.1% | 0.6 | 0.587 |
| 0.16 | 22485 | 22034 | 22259 | 1.4% | 0.1 | 0.916 |
| 0.13 | 21217 | 22037 | 21627 | 2.7% | 0.1 | 0.890 |
| 0.44 | 13497 | 12803 | 13150 | 3.7% | 0.7 | 0.541 |
| 1.22 | 10579 | 10513 | 10546 | 0.4% | 1.1 | 0.434 |
| 5.97 | 608 | 577 | 593 | 3.7% | 4.9 | 0.024 |
| 2.17 | 5091 | 5307 | 5199 | 2.9% | 2.3 | 0.214 |
| 0.60 | 12086 | 12656 | 12371 | 3.3% | 0.8 | 0.509 |
| 0.51 | 10556 | 10300 | 10428 | 1.7% | 1.1 | 0.429 |
| 3.91 | 1467 | 1594 | 1530 | 5.9% | 4.2 | 0.063 |
| 1.10 | 14054 | 13882 | 13968 | 0.9% | 0.6 | 0.575 |
| 1.00 | 14052 | 12296 | 13174 | 9.4% | 0.7 | 0.542 |
| 2.24 | 2069 | 2267 | 2168 | 6.4% | 3.7 | 0.089 |
| 0.00 | 24224 | 24385 | 24305 | 0.5% | #NUM! | 1.000 |

Example 3

Example 3 describes a simultaneous assay of a sample for both $T_3$ and $T_4$ using two phycoerythrin conjugates (III and VI). The microparticles used in the invention are coated with either anti-$T_3$ or anti-$T_4$ antibody. The particles are suspended in particle diluent consisting of 50 mM phosphate buffered saline (PBS), 1% prionex, 0.1% $NaN_3$. 0.1% and Tween at pH 7.4. The wash buffer consists of 50 mM PBS, 0.5% BGG, 0.1% $NaN_3$ and 0.1% Tween at pH 7.4.

3a Two Conjugates, Simultaneous Assay (N-acetyl-3-iodotyrosine (VI) and FMOC,3,5, diiodotyrosine (III)

Sample (100 µL) was added to 100 µL reagent particles (Micromods 8 µm, (a) 10 µg/cm$^3$ anti-$T_3$ antibody; (b) 7.5 µg/cm$^2$ anti-$T_4$ antibody). The resulting mixture was incubated for 15 minutes at 37° C. with agitation. The particles were submitted to a magnetic separation phase for 3 minutes, after which the solution was removed by aspiration. To the particles was added wash buffer (300 µL), the particles were magnetically separated and the solution was removed by aspiration. The wash process was repeated twice, after which the particles were again magnetically separated and the fluid was removed by aspiration.

To the particles prepared as described above was added a mixture (50 µL) of N-acetyl-3-iodotyrosine-PE conjugate and FMOC-3,5-diiodotyrosine-PE conjugate. Stock solutions of the conjugates were diluted in conjugate diluent (50 mM PBS, 0.5% BGG, 2.75% PEG 8000, 0.1% $NaN_3$ and 0.1% Tween, at pH 7.4) as follows: the N-acetyl-3-iodotyrosine-PE (stock, 2.8×10$^{-6}$ M) was diluted 1/40 and the FMOC 3,5-diiodotyrosine-PE (stock, 4.4×10$^{-6}$ M) was diluted 1:10. The resulting mixture was incubated for 15 minutes at 37° C. with agitation. The particles were magnetically separated for 3 minutes and the fluid was removed by aspiration. Wash buffer (300 µL) was added, the particles were submitted to magnetic separation and the wash buffer was removed by aspiration. The wash cycle was repeated twice. The buffer from the final wash was removed by aspiration and the particles were resuspended in wash buffer (35 µL) and read on Luminex LX100.

3b Results

Figure 2A:
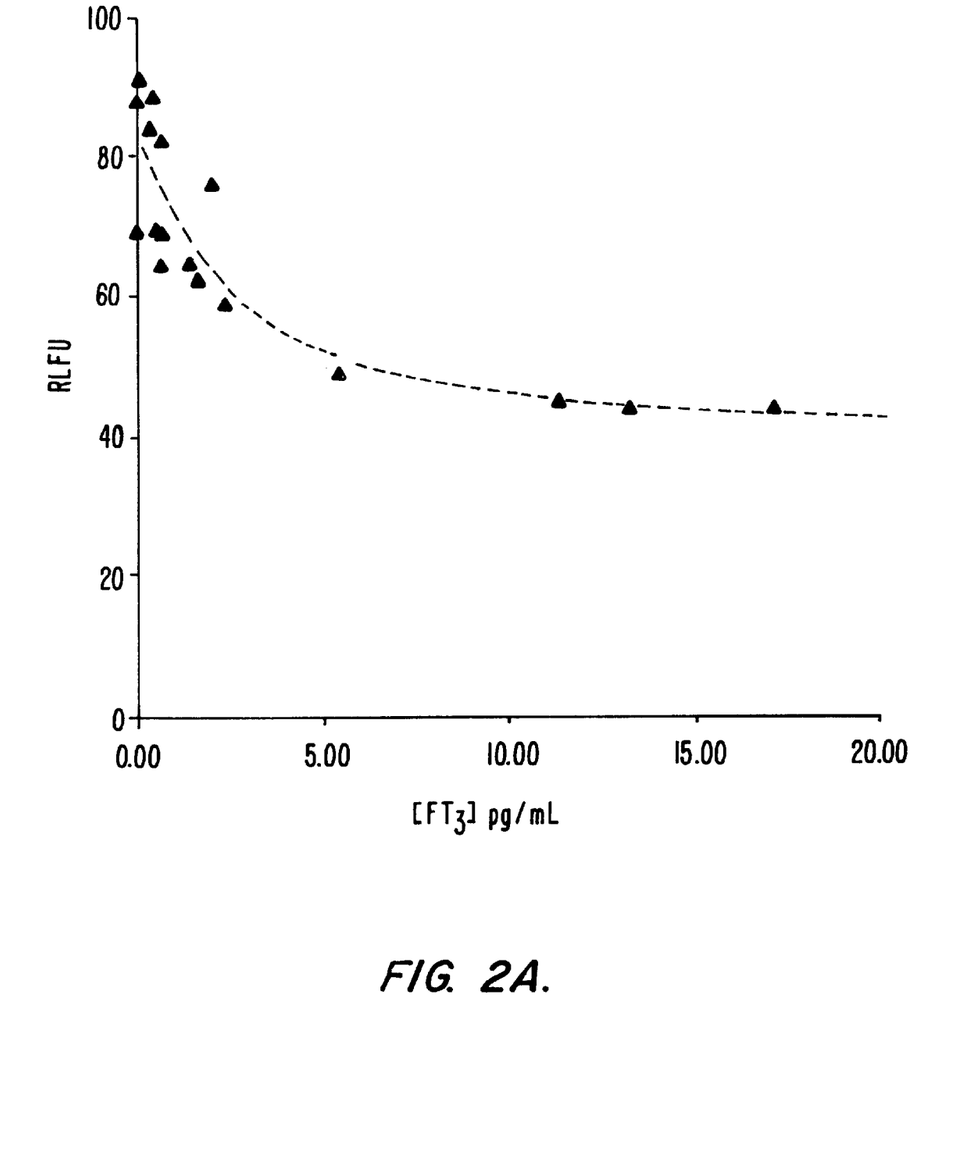
Figure 2B:
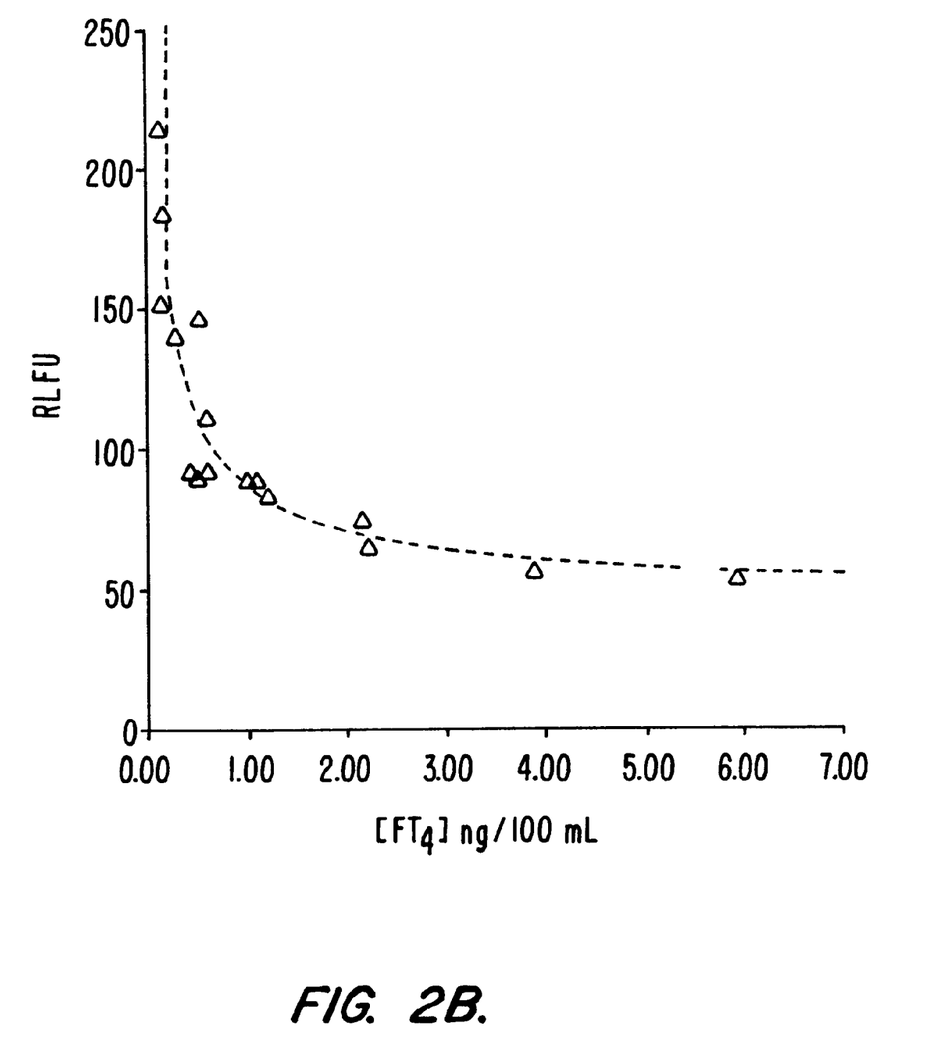

The results of the simultaneous dual conjugate assay for $T_4$ and $T_3$ are set forth graphically in FIG. 2A and FIG. 2B, respectively. Table 3 and Table 4 set forth results for the $T_3$ and $T_4$ content of the sample, respectively, as determined by a method of the invention, and provide a comparison with a radioactive immunoassay technique (RIA).

TABLE 3

| DPC RIA | Rep 1 | Rep 2 | Mean | % CV | [FT3] ng/100 mL | B/Bo |
|---|---|---|---|---|---|---|
| 0.41 | 88 | 89 | 89 | 0.8% | #NUM/! | 0.973 |
| 0.00 | 74 | 65 | 69 | 8.7% | 1.2 | 0.761 |
| 0.00 | 88 | 88 | 88 | 0.4% | #NUM/! | 0.964 |
| 0.68 | 84 | 81 | 82 | 3.0% | 0.1 | 0.904 |
| 0.05 | 93 | 89 | 91 | 3.1% | #NUM/! | 1.000 |
| 0.34 | 84 | 84 | 84 | 0.0% | #NUM/! | 0.923 |
| 1.43 | 64 | 66 | 65 | 2.7% | 1.8 | 0.712 |
| 1.99 | 61 | 91 | 76 | 27.9% | 0.6 | 0.835 |
| 17.08 | 43 | 45 | 44 | 3.2% | 14.1 | 0.484 |
| 11.35 | 43 | 47 | 45 | 6.3% | 11.7 | 0.495 |
| 1.65 | 62 | 63 | 63 | 1.1% | 2.1 | 0.687 |
| 2.33 | 59 | 59 | 59 | 0.0% | 2.8 | 0.648 |
| 13.19 | 44 | 44 | 44 | 0.0% | 14.1 | 0.484 |
| 0.69 | 71 | 67 | 69 | 4.1% | 1.3 | 0.758 |
| 0.63 | 64 | 65 | 65 | 1.1% | 1.8 | 0.709 |
| 5.39 | 47 | 51 | 49 | 5.8% | 6.8 | 0.538 |
| 0.50 | 68 | 71 | iO | 3.1% | 1.2 | 0.764 |

TABLE 4

| DPC RIA | Rep 1 | Rep 2 | Mean | % CV | [FT4] ng/100 mL | B/Bo |
|---|---|---|---|---|---|---|
| 0.52 | 152 | 140 | 146 | 5.6% | 0.2 | 0.683 |
| 0.29 | 153 | 127 | 140 | 13.4% | 0.3 | 0.655 |
| 0.15 | 155 | 148 | 152 | 3.3% | 0.2 | 0.710 |
| 0.59 | 111 | 111 | 111 | 0.0% | 0.5 | 0.520 |
| 0.16 | 187 | 181 | 184 | 2.3% | 0.1 | 0.862 |
| 0.13 | 212 | 215 | 214 | 1.0% | 0.1 | 1.000 |
| 0.44 | 91 | 92 | 92 | 0.8% | 0.8 | 0.429 |
| 1.22 | 83 | 83 | 83 | 0.0% | 1.1 | 0.389 |
| 5.97 | 53 | 55 | 54 | 2.6% | 7.6 | 0.253 |
| 2.17 | 74 | 73 | 74 | 1.0% | 1.7 | 0.344 |
| 0.60 | 93 | 92 | 93 | 0.8% | 0.8 | 0.433 |
| 0.51 | 91 | 86 | 89 | 4.0% | 0.9 | 1.000 |
| 3.91 | 56 | 57 | 57 | 1.3% | 5.7 | 0.265 |
| 1.10 | 89 | 87 | 88 | 1.6% | 0.9 | 0.412 |
| 1.00 | 86 | 91 | 89 | 4.0% | 0.9 | 0.415 |
| 2.24 | 65 | 65 | 65 | 0.0% | 2.8 | 0.304 |
| Sipac 0 | 96 | 101 | 99 | 3.6% | 0.7 | 0.461 |

Example 4

Example 4 describes a sequential assay of a sample for both $T_3$ and $T_4$ using two phycoerythrin conjugates of the invention (III and VI). The microparticles used in the invention are coated with either anti-$T_3$ or anti-$T_4$ antibody. The particles are suspended in particle diluent consisting of 50 mM phosphate buffered saline (PBS), 1% prionex, 0.1% $NaN_3$ and 0.1% Tween at pH 7.4. The wash buffer consists of 50 mM PBS, 0.5% BGG, 0.1% $NaN_3$ and 0.1% Tween at pH 7.4.

4a $T_3$ and $T_4$ Sequential Assay

To 100 µL of sample are added N-acetyl-3-iodotyrosine-PE conjugate (50 µL, stock (2.8×10$^{-6}$ M) diluted 1:20 in 50 mM PBS, 1% prionex, 2.75% PEG 8000, 0.1% $NaN_3$ and 0.1% Tween) and 100 µL reagent particles (Micromods 8 µm, (a) 20 µg/cm$^2$ anti-$T_3$ antibody; (b) 7.5 µg/cm2 anti-$T_4$ antibody). The resulting mixture was incubated for 15 minutes at 37° C. with agitation. The particles were submitted to a magnetic separation phase for 3 minutes, after which the solution was removed by aspiration. To the particles was added wash buffer (300 μL), the particles were magnetically separated and the solution was removed by aspiration. The wash process was repeated twice, after which the particles were again magnetically separated and the fluid was removed by aspiration.

To the particles prepared as described above was added FMOC-3,5-diiodotyrosine-PE conjugate (50 μL, stock (4.4× $10^{-6}$ M) diluted 1:5 in 50 mM PBS, 1% prionex, 2.75% PEG 8000, 0.1% $NaN_3$ and 0.1% Tween)). The resulting mixture was incubated for 15 minutes at 37° C. with agitation. The particles were magnetically separated for 3 minutes and the fluid was removed by aspiration. Wash buffer (300 μL) was added, the particles were submitted to magnetic separation and the wash buffer was removed by aspiration. The wash cycle was repeated twice. The buffer from the final wash was removed by aspiration and the particles were resuspended in wash buffer (35 μL) and read on Luminex LX100.

4b Results

Figure 3A:
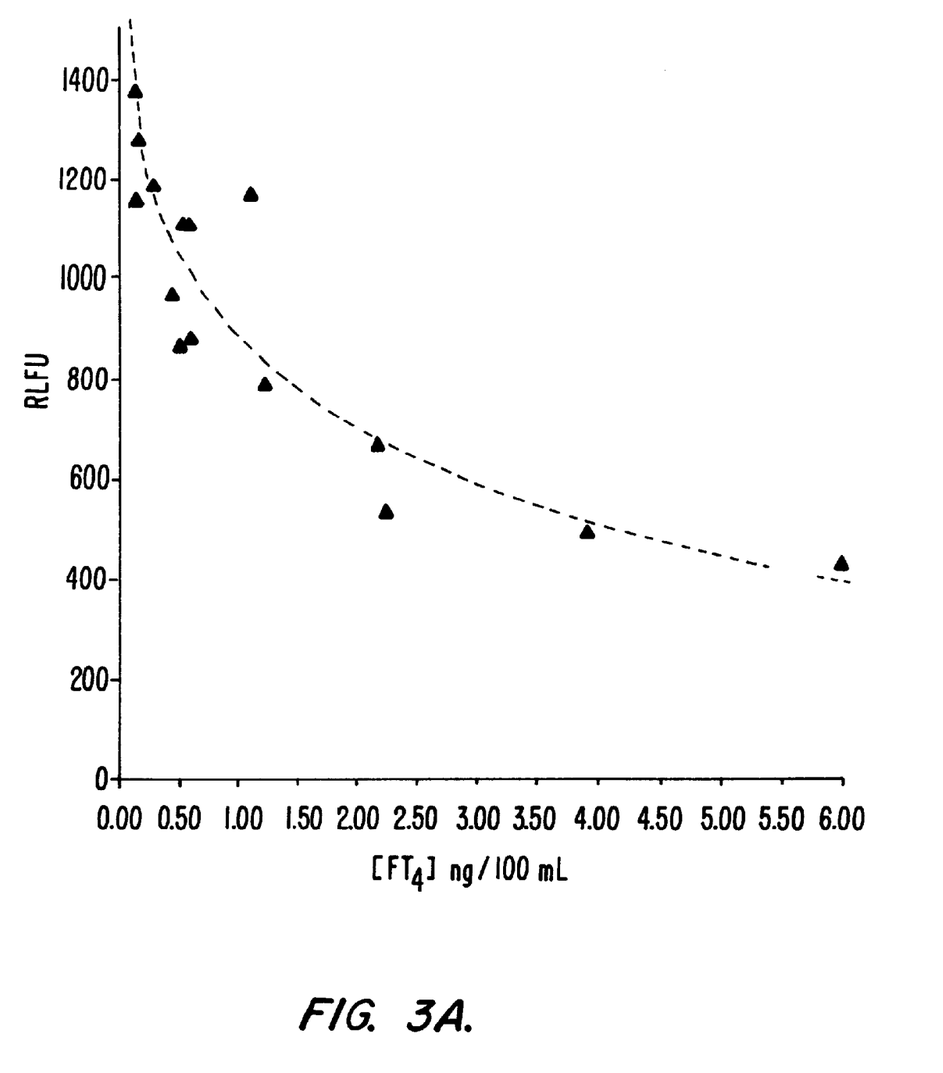
Figure 3B:
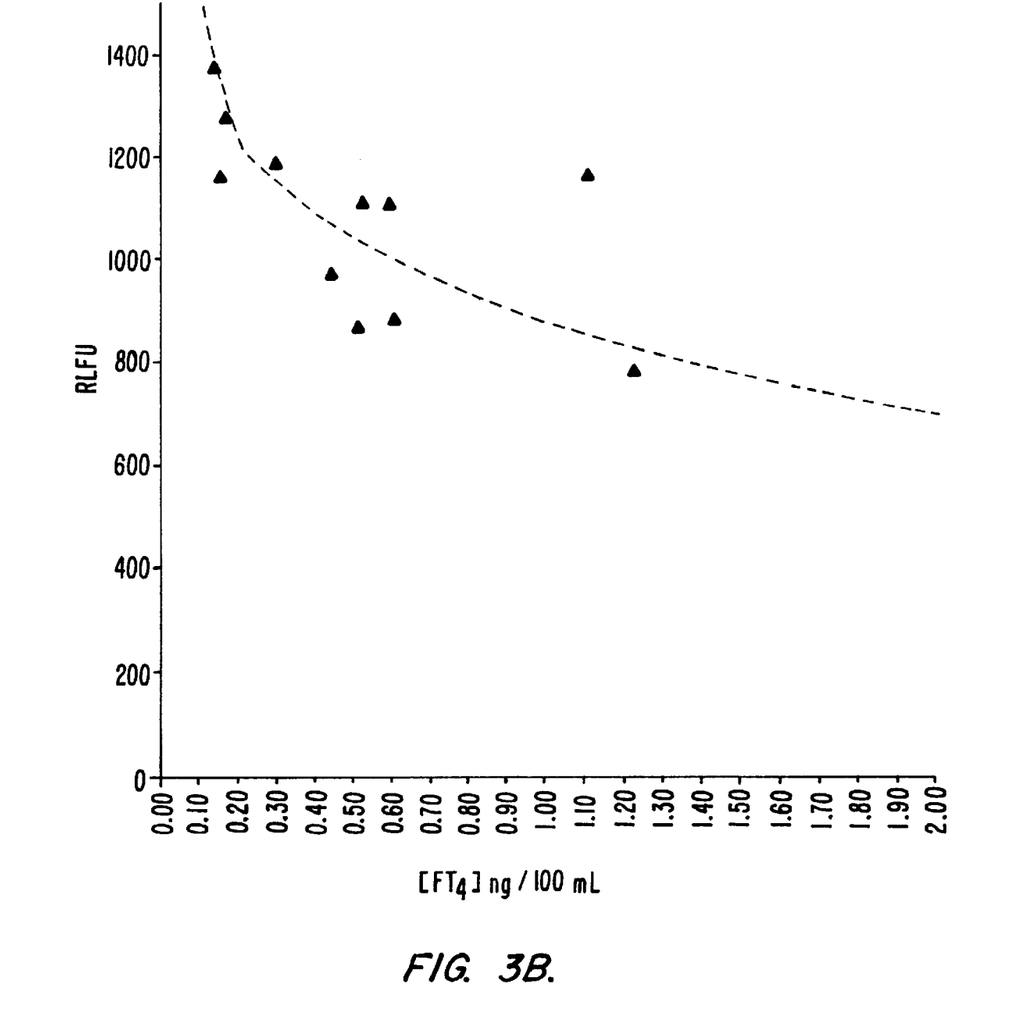
Figure 3C:
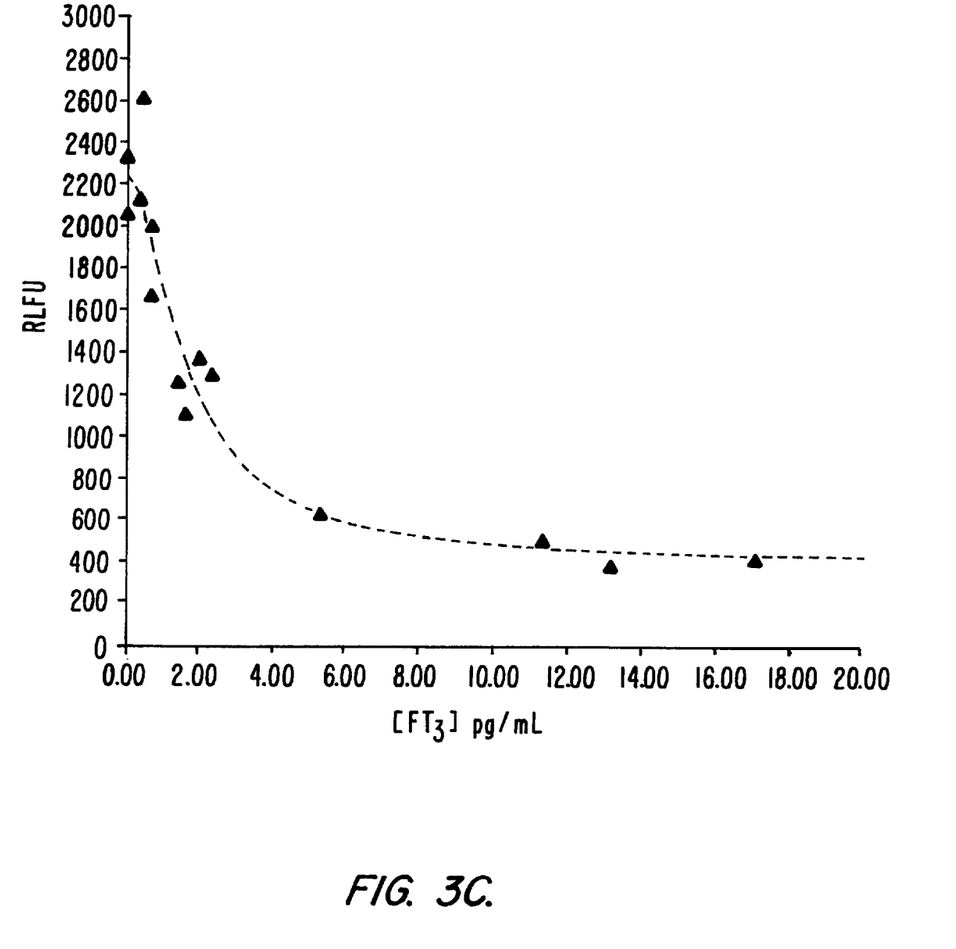
Figure 3D:
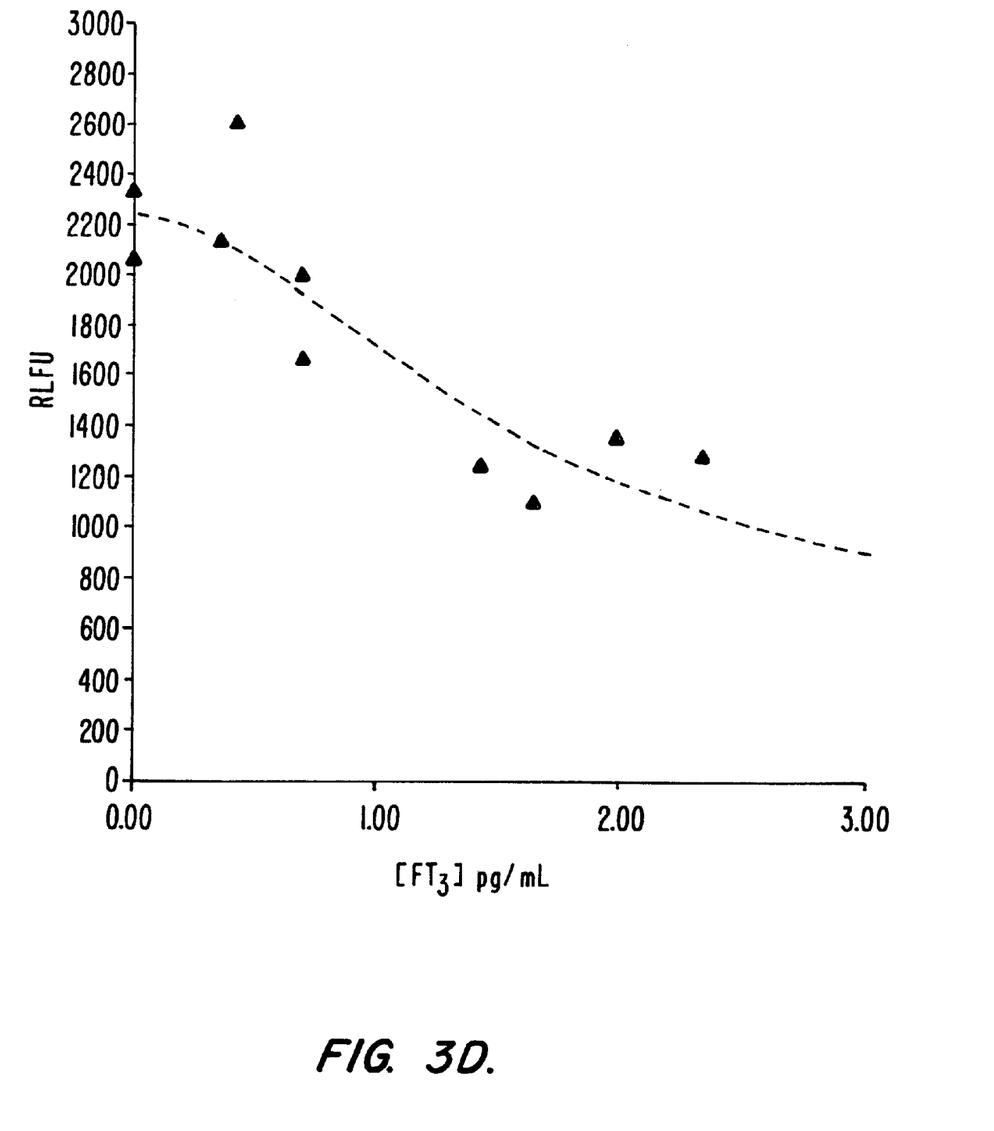

The results of the simultaneous dual conjugate assay for $T_4$ and $T_3$ are set forth graphically in FIG. 3A and FIG. 3B, respectively. Table 5 and Table 6 set forth results for the $T_3$ and $T_4$ content of the sample, respectively, as determined by a method of the invention, and provide a comparison with a radioactive immunoassay technique (RIA).

TABLE 5

| DPC RIA | Rep 1 | Rep 2 | Mean | % CV | [$FT_3$] ng/100 mL | B/Bo |
|---|---|---|---|---|---|---|
| 0.41 | 2636 | 2590 | 2613 | 1.2% | #NUM/! | 4.175 |
| 0.00 | 2015 | 2107 | 2061 | 3.2% | 0.5 | 3.293 |
| 0.00 | 2107 | 2024 | 2065 | 2.8% | 0.5 | 3.300 |
| 0.68 | 2080 | 1926 | 2003 | 5.4% | 0.6 | 3.200 |
| 0.00 | 2389 | 2286 | 2337 | 3.1% | #NUM/! | 3.735 |
| 0.34 | 2056 | 2218 | 2137 | 5.3% | 0.3 | 3.415 |
| 1.43 | 1204 | 1311 | 1257 | 6.0% | 1.8 | 2.009 |
| 1.99 | 1388 | 1364 | 1376 | 1.2% | 1.6 | 2.198 |
| 17.08 | 400 | 440 | 420 | 6.7% | 26.5 | 0.671 |
| 11.35 | 489 | 513 | 501 | 3.4% | 9.0 | 0.801 |
| 1.65 | 1161 | 1059 | 1110 | 6.5% | 2.2 | 1.773 |
| 2.33 | 1375 | 1219 | 1297 | 8.5% | 1.7 | 2.072 |
| 13.19 | 386 | 384 | 385 | 0.4% | #NUM! | 0.615 |
| 0.69 | 1643 | 1700 | 1671 | 2.4% | 1.1 | 2.671 |
| 5.32 | 616 | 636 | 626 | 2.2% | 5.3 | 1.000 |
| 0 $FT_3$ | 7234 | 6615 | 6925 | 6.3% | #NUM! | 1.000 |
| 0 $FT_4$ | 6574 | 6282 | 6428 | 3.2% | #NUM! | 1.000 |

TABLE 6

| DPC RIA | Rep 1 | Rep 2 | Mean | % CV | [$FT_4$] ng/100 mL | B/Bo |
|---|---|---|---|---|---|---|
| 0.52 | 1124 | 1096 | 1110 | 1.8% | 0.4 | 0.253 |
| 0.29 | 1231 | 1146 | 1189 | 5.1% | 0.2 | 0.271 |
| 0.15 | 1175 | 1146 | 1161 | 1.8% | 0.3 | 0.264 |
| 0.59 | 1123 | 1091 | 1107 | 2.0% | 0.4 | 0.252 |
| 0.16 | 1299 | 1261 | 1280 | 2.1% | 0.1 | 0.292 |
| 0.13 | 1400 | 1355 | 1377 | 2.3% | 0.1 | 0.314 |
| 0.44 | 944 | 997 | 970 | 3.8% | 0.7 | 0.221 |
| 1.22 | 787 | 787 | 787 | 0.0% | 1.4 | 0.179 |
| 5.97 | 393 | 466 | 430 | 12.0% | 5.3 | 0.098 |
| 2.17 | 657 | 684 | 671 | 2.8% | 2.2 | 0.153 |
| 0.60 | 812 | 954 | 883 | 11.4% | 1.0 | 0.201 |
| 0.51 | 897 | 840 | 869 | 4.6% | 1.0 | 0.198 |
| 3.91 | 503 | 486 | 495 | 2.4% | 4.2 | 0.113 |
| 1.10 | 1169 | 1167 | 1168 | 0.1% | 0.3 | 0.266 |
| 2.24 | 527 | 532 | 529 | 0.6% | 3.7 | 0.121 |
| 0 $FT_4$ | 4197 | 4579 | 4388 | 6.2% | #NUM! | 1.000 |
| 0 $FT_3$ | 5079 | 4827 | 4953 | 3.6% | #NUM! | 1.000 |

It is understood that the examples and embodiments described herein are for illustrative purposes only and that various modifications or changes in light thereof will be suggested to persons skilled in the art and are to included within the spirit and purview of this application and are considered within the scope of the appended claims. All publications, patents, and patent applications cited herein are hereby incorporated by reference in their entirety for all purposes.

What is claimed is:

1. A compound having a structure selected from the group consisting of

, and wherein PBP is a phycobiliprotein.

2. The compound according to claim 1 wherein, said phycobiliprotein is phycoerythrin.

3. A method for individually determining the amount of $T_3$ and $T_4$ thyroid hormone in a biological sample using a competitive immunoassay, said method comprising:

(a) contacting said biological sample with a plurality of microparticles classifiable into a first population and a second population distinguishable from each other by an automated detection means, said first population having an anti-$T_3$ antibody coupled thereto and said second population having an anti-$T_4$ antibody coupled thereto, and a fluorescent thyroid hormone analogue which is a member selected from the group consisting of to form an assay mixture;

(b) recovering said microparticles from said assay mixture;

(c) detecting fluorescence from said first and second population independently and correlating said fluorescence thus detected with said first and second populations, thereby determining the amount of $T_3$ thyroid hormone and $T_4$ thyroid hormone in said sample.

4. The method according to claim 3, wherein said fluorescent probe is compound V.

5. The method according to claim 3, wherein said fluorescent probe is a mixture of compounds III and IV.

6. The method according to claim 5, wherein said microparticles are contacted with compounds III and IV simultaneously.

7. The method according to claim 5, wherein said microparticles are contacted with compounds III and IV sequentially.

8. The method according to claim 3, wherein said fluorescent probe is a mixture of compounds III and VI.

9. The method according to claim 8, wherein said microparticles are contacted with compounds III and VI simultaneously.

10. The method according to claim 8, wherein said microparticles are contacted with compounds III and VI sequentially.

11. The method according to claim 3, wherein said microparticles are magnetically responsive particles.

* * * * *